(12) United States Patent
Haeberlin et al.

(10) Patent No.: US 6,306,900 B1
(45) Date of Patent: *Oct. 23, 2001

(54) ENTERIC COATED PHARMACEUTICAL COMPOSITIONS

(75) Inventors: Barbara Haeberlin, Riehen; Ching-Pong Mak, Therwil, both of (CH); Armin Meinzer, Buggingen (DE); Jacky Vonderscher, Riedisheim (FR)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/694,209

(22) Filed: Oct. 23, 2000

Related U.S. Application Data

(62) Continuation of application No. 09/469,536, filed on Dec. 22, 1999, now Pat. No. 6,172,107, which is a continuation of application No. 09/077,398, filed as application No. PCT/EP97/01800 on Apr. 10, 1997, now Pat. No. 6,025,391.

(30) Foreign Application Priority Data

Apr. 12, 1996 (GB) .................................. 9607564
Oct. 24, 1996 (GB) .................................. 9622028

(51) Int. Cl.$^7$ .......................... A61K 31/34; A01N 43/08
(52) U.S. Cl. .................. 514/470; 514/8; 514/11; 514/570; 514/576; 514/885; 514/960; 514/968; 424/457; 424/458; 424/459; 424/461; 424/462; 424/463; 424/468; 424/474; 424/475; 424/479; 424/480; 424/482; 424/490; 424/493; 424/494; 424/495; 424/497
(58) Field of Search .................... 514/470, 8, 11, 514/570, 576, 885, 960, 968; 424/457, 458, 459, 461, 462, 463, 468, 474, 475, 479, 480, 482, 490, 493, 494, 495, 497

(56) References Cited

U.S. PATENT DOCUMENTS

| | | | |
|---|---|---|---|
| 3,705,894 | 12/1972 | Gerzon et al. | 260/240 |
| 3,705,946 | 12/1972 | Dyke et al. | 424/279 |
| 3,777,020 | 12/1973 | Johnson | 424/180 |
| 3,825,571 | 7/1974 | Mori et al. | 260/343.3 |
| 3,853,919 | 12/1974 | Mori et al. | 260/343.3 |
| 3,868,454 | 2/1975 | Johnson | 424/248 |
| 3,880,995 | 4/1975 | Jones | 424/180 |
| 3,903,071 | 9/1975 | Holmes | 260/210 |
| 4,005,108 | 1/1977 | Kupchan et al. | 260/343 R |
| 4,234,684 | 11/1980 | Abbott et al. | 435/75 |
| 4,680,299 | 7/1987 | Hesson | 514/311 |
| 4,686,234 | 8/1987 | Nelson et al. | 514/469 |
| 4,725,622 | 2/1988 | Nelson et al. | 514/469 |
| 4,727,069 | 2/1988 | Nelson et al. | 514/211 |
| 4,753,935 | 6/1988 | Nelson et al. | 514/233.5 |
| 4,786,637 | 11/1988 | Allison et al. | 514/233.5 |
| 4,808,592 | 2/1989 | Nelson et al. | 514/233.5 |
| 4,847,381 | 7/1989 | Sutherland et al. | 546/156 |
| 4,868,153 | 9/1989 | Allison et al. | 514/470 |
| 4,959,387 | 9/1990 | Nelson et al. | 524/469 |
| 4,992,467 | 2/1991 | Allison et al. | 514/464 |

FOREIGN PATENT DOCUMENTS

| | | |
|---|---|---|
| 815330 | 5/1973 | (BE) . |
| 0281713 | 9/1988 | (EP) . |
| 551182 | 7/1993 | (EP) . |
| 0691130 | 1/1996 | (EP) . |
| 1157099 | 7/1969 | (GB) . |
| 1157100 | 7/1969 | (GB) . |
| 1158387 | 7/1969 | (GB) . |
| 1203328 | 8/1970 | (GB) . |
| 1261060 | 1/1972 | (GB) . |
| 2117238 | 10/1983 | (GB) . |
| 94/01105 | 1/1994 | (WO) . |
| 94/26265 | 11/1994 | (WO) . |
| 94/26266 | 11/1994 | (WO) . |
| 95/04627 | 4/1995 | (WO) . |
| 95/09626 | 4/1995 | (WO) . |
| 95/13082 | 5/1995 | (WO) . |
| 31237 | 11/1967 | (ZA) . |

OTHER PUBLICATIONS

Sweeney et al., Cancer Research 32, pp. 1803–1809, Sep. 1972.
JF Bach et al. The mode of action of immunosuppressive agents, Elsevier Publisher, Amsterdam, 1985, pp. 105–174.
Allison et al., Springer Semin Immunopathol (1993) 14:353–380.
Epinette et al. Journal of the American Academy of Dermatology, pp. 962–971, 1978.
Ohsugi et al. Cancer Research 36, pp. 2923–2927, Aug. 1976.
Franklin et al., Biochem. J. (1969), vol. 113, pp. 515–524.
Mitsui et al., CA 75;150091, Progr. Antimicrob. Anticancer Chemother., Proc. Int. Congr. Chemother., $6^{th}$ (1970) vol. 2, pp. 130–135.
Schiantarelli et al. Agents and Actions, vol. 14, No. 2 (1984) pp. 247–256.
Suzuki et al. The Journal of Antibiotics, vol. XXIX, No. 3, pp. 275–285, 1980.
Harrison et al. J.C.S. Perkins II, pp. 1542–1544, 1985.
Seki et al. Antimicrobial Agents and Chemotherapy, vol. 33, No. 5, May 1989, pp. 773–775.
Allison et al. In: Immunosuppressive Drugs–Development in anti–rejection therapy, pp. 141–159, 1988.
Mitsui et al., The Journal of Antibiotics, Aug. 1969, pp. 358–363.
James J. Lipsky, The Lancet 1996; vol. 348, Nov. 16, 1996, pp. 1357–1359.
H. Boxenbaum, Journal of Pharmacokinetics and Biopharmaceutics, vol. 10, No. 2, 1982, pp. 201–227.

(List continued on next page.)

*Primary Examiner*—Frederick Krass
(74) *Attorney, Agent, or Firm*—John D. Thallemer

(57) ABSTRACT

This invention provides a pharmaceutical composition comprising a mycophenolate salt, the composition being adapted to release mycophenolate in the upper part of the intestinal tract.

14 Claims, No Drawings

OTHER PUBLICATIONS

Eugui et al. Scand. J. Immunol. 33, pp. 175–183, 1991.
Morris et al. Transplant. Proc. vol. 22, pp. 1659–1662 (1990).
Lee et al., Pharmaceutical Research, vol. 7, No. 2, 1990, pp. 161–165.
Boit, Beilsteins Handbuch der Organischem Chemi, vol. 18, Part 7, p. 6513, 1990.
Luckenbach, Beilstein Handbook of Organic Chemistry, vol. 18, Part 9, p. 239, 1992.
Makara et al., CA 124:139508 (abstract of Journal Med. Chem. 1996, 39, pp. 1236–1242.
Suzuki et al., CA BA62:38453, The Journal of Antibiotics, Mar. 1976, vol. 29, No. 3, pp. 286–291.
Potel, Aus der Bakteriologischen Forschungsabteilung der Asta–Werke AG., pp. 527–532, 1977.
XP 002043101 Fester orale and perorate Arzneiformen, pp. 356–361, 1974.
Nature, vol. 223, Aug. 23, 1969, pp. 848–850.
Aisenberg, The New England Journal of Medicine, May 27, 1965, pp. 1114–1116.
Marinari et al., XP 002043018, Arch Dermatol, vol. 113, Jul. 1977, pp. 930–931.
XP002043019, European Mycophenolate Mofetil Cooperative Study Group, vol. 345, May 27, 1995, pp. 1321–1322.
80538 Chemical Abstracts vol. 73, 1970, p. 230, No. 80540w.
Chemical Abstracts, vol. 80, 1974, p. 338, No. 59722s.
Chemical Abstract, vol. 80, 1974, p. 420, No. 120748y.
Chemical Sbstract, vol. 96, 1982, p. 646, No. 199422x.
Chemical Abstract 7–Enzymes, vol. 124, Nov. 11, 1996, p. 559, No. 139508w.
26–Biomolecules, vol. 96, 1982, p. 647.
Chemical Abstract, vol. 98, 1983, p. 564, No. 143262w.
Chemical Abstract, vol. 98, 1983, p. 632, No. 198004w.
27 Heterocytes, vol. 98, 1983, p. 565.
Schnitzer, Academic Press, vol. 10, 1972, pp. 14–19, 24, 25, 70 and 71.
The Lancet, vol. 345, May 27, 1995, pp. 1323–1325.
Sollinger, H.W., Chem. Abstr. 1996, 95370774, Kidney Int'l, Supplement, 1995, vol. 52, pp. 514–517.
Platz et al., "A new and potent immunosuppressive agent, "Transplantation, vol. 51, No. 1, 1991, pp. 27–31.
Ohsugi, et al., "Antitumor and immunosuppressive effects of mycophenolic acid derivatives", Cancer Rres. vol. 36, No. 1976, pp. 2923–2927.
Chemical Abstract 108174f, Gerzon et al., "Mycophenolic acid and its derivatives, inhibitors of malignant tumor cell growth in warm–blooded mammals", 1976.
Ito et al., Pharmacokinetics of Mycophenolic Acid in Healthy Human Voluteers, J. Med. Soc. Toho, Japan, vol. 29, No. 3, 1982, pp. 412–418.
Kajiwara et al., General Pharmacology of Mycophenolic Acid, J. Med. Soc. Toho, Japan, vol. 29, No. 3, 1982, pp. 419–425.
Kajiwara et al., Species Differences of Mycophenolic Acid, a New Drug for Psoriasis in Acute, Sub–acute and Chronic Toxicity, Journal of the Medical Society of Toho University, Sep. 1, 1982.
Ohsugi et al., CA84:103774, Areugi, (1975) 24 (12) pp. 820–825.
Hasunuma, et al., CA 112:191604 Abstract of Adv. Exp. Med. Biol. (1989) 253A (Purine Pyrimidine Metab. Man 6, Pt. A), pp.455–460.
Derwent Abstract 93–329920/41 corresponding to JP 06256182–A (1994).
Derwent Abstract 94–313614/39 corresponding to JP 06239740–A (1994).
Derwent Abstract 93–220931/28 corresponding to EP 551182–A1 (1993).
Derwent Abstract 84509V/49 corresponding to BE 815–330 (1974).
Derwent Abstract 37140T–B corresponding to BE 775785 (1972).
Derwent Abstract 88322 C/49 corresponding to US 4234–684 (1980).

ENTERIC COATED PHARMACEUTICAL COMPOSITIONS

This application is a continuation of U.S. application Ser. No. 09/469,536, filed Dec. 22, 1999, now U.S. Pat. No. 6,172,107 which is a continuation of U.S. application Ser. No. 09/077,398, filed May 28, 1998, now U.S. Pat. No. 6,025,391 which is a 371 of PCT/EP97/01800, filed Apr. 10, 1997.

This invention relates to mycophenolic acid.

Mycophenolic acid, also referred to herein as MPA, was first isolated in 1896, and has been extensively investigated as a pharmaceutical of potential commercial interest. It is known to have anti-tumor, anti-viral, immunosuppressive, anti-psoriatic, and anti-inflammatory activity [see e.g. W. A. Lee et al, Pharmaceutical Research (1990), 7, p. 161–166 and references cited therein]. Publications have appeared on MPA as an anti-cancer agent by Lilly scientists, see e.g. M. J. Sweeney et al., Cancer Research (1972), 32, 1795–1802, and by ICI scientists, see e.g. GB 1,157,099 and 1,203,328 and as an immunosuppressant agent see e.g. A. Mitsui et al. J. Antibiotics (1969) 22, p. 358–363. In the above-mentioned article by W. A. Lee et al it is stated that attempts have been made to increase the bio-availability or specificity of MPA by making derivatives. The poor bioavailability of the acid was thought to be caused by undetermined factors such as drug complexation in the gastro-intestinal lumen, a narrow absorption window, metabolism before absorption etc.. The preparation of the morpholinoethyl ester, also known as mycophenolate mofetil (sometimes referred to herein as MMF), was described which had considerably higher bioavailability than MPA (100% for MMF and 43% for MPA). This derivative has been recently introduced commercially as an immunosuppressant for the treatment or prevention of organ or tissue transplant rejection, at daily dosages of from about 200 mg to about 3 grams p.o, e.g. about 2 g p.o. Patient compliance with MMF is not ideal, inter alia, because of side-effects e.g. gastro-intestinal side effects, the origin of which is not known.

We have now found, after exhaustive testing, that mycophenolate salts when enteric coated or adapted to be released in the upper part of the intestines, e.g. in the duodenum, jejeunum and/or ileum, are effective, well-tolerated, pharmaceuticals particularly for immunosuppressive indications especially for the treatment or prevention of organ, tissue or cellular allograft or xenograft rejection, e.g. after transplant, or the treatment or prevention of immune-mediated diseases (autoimmune diseases) and have interesting bioavailability and stability characteristics. Moreover fewer unit dosage forms are required to be administered than for MMF, leading to easier administration.

The present invention provides in one aspect a pharmaceutical composition comprising a myophenolate salt, the composition being adapted to release mycophenolate in the upper part of the intestinal tract (hereinafter referred to as a composition of the invention). The composition may be adapted in any conventional manner, preferably with means adapted to prevent release of the myocophenolate in the stomach and to ensure release in the upper part of the intestinal tract. In a further aspect the invention provides a pharmaceutical composition comprising a coated pharmaceutically acceptable mycophenolate salt.

Such salts are cationic salts, e.g. of alkali metals, especially the sodium salts. Sodium mycophenolate salts are known, e.g. in South African Patent 68/4959. We prefer to use the mono-sodium salt. This may be obtained in crystalline form by recrystallization from acetone/ethanol if necessary with water; Mpt. 189–191° C.

The invention provides, more specifically, a solid enteric-coated composition in unit dose form for oral application, the core of the composition containing sodium mycophenolate in solid or liquid form.

The term "core" comprises sodium mycophenolate (or other cationic salt) if desired in admixture with further physiologically acceptable material, that can be surrounded by an enteric-coating. The term "core" comprises, in a wide sense, not only tablets, pellets or granules but also capsules, e.g. soft or hard capsules of gelatine or starch. Such cores may be produced in conventional manner. We have found that the mycophenolate salts, particularly the sodium salt, are particularly interesting for the production of tablets. When tablet cores are used they have preferably a hardness of from ca. 10 to 70 N.

The pellets or granules may, after application of the enteric-coating as described hereinafter may be used as such or to fill capsules, e.g. hard gelatine capsules. If desired the capsules may be alternatively enteric-coated, e.g. in conventional manner.

Other pharmaceutically acceptable ingredients may be present in the cores, e.g. those conventionally used in the preparation of pharmaceutically compositions, e.g. fillers, e.g. lactose, glidants, e.g. silica, and lubricants, e.g. magnesium stearate.

The term "enteric coating" comprises any pharmaceutically acceptable coating preventing the release of the active agent in the stomach and sufficiently disintegrating in the intestine tract (by contact with approximately neutral or alkaline intestine juices) to allow the resorption of the active agent through the walls of the intestinal tract. Various in vitro tests for determining whether or not a coating is classified as an enteric coating have been published in the pharmacopoeia of various countries.

More specifically, the term "enteric coating" as used herein refers to a coating which remains intact for at least 2 hours, in contact with artificial gastric juices such as HCl of pH 1 at 36 to 38° C. and preferably thereafter disintegrates within 30 minutes in artificial intestinal juices such as a $KH_2PO_4$ buffered solution of pH 6.8.

The thickness of the coating may vary and depends inter alia on its permeability in water and acids. A typical coating may be about 16–30, e.g. 16–20 or to 25, mg on a size 1 gelatine capsule. Similar thicknesses may be applied in other formulations.

In general satisfactory results are obtained with a coating of 5–100 μm, preferably 20–80 μm thickness. The coating is suitably selected from macromolecular polymers. Suitable polymers are listed in e.g. L. Lachman et al. The Theory and Practice of Industrial Pharmacy, 3rd Ed, 1986, p. 365–373, H. Sucker et al, Pharmazeutische Technologie, Thieme, 1991. p. 355–359, Hagers Handbuch der pharmazeutischen Praxis, 4th Ed. Vol. 7, pages 739 to 742 and 766 to 778, (Springer Verlag, 1971) and Remington's Pharmaceutical Sciences, 13th Ed., pages 1689 to 1691 (Mack Publ., Co., 1970) and comprise e.g. cellulose ester derivatives, cellulose ethers, acrylic resins, such as methylacrylate copolymers and copolymers of maleic acid and phthalic acid derivatives.

The preferred films are made from cellulose acetate phthalate and trimellitate; methacrylic acid copolymers, e.g. copolymers derived from methylacrylic acid and esters thereof, containing at least 40% methylacrylic acid; and especially hydroxypropyl methylcellulose phthalate.

Methylacrylates include those of molecular weight above 100,000 daltons based on, e.g. methylacrylate and methyl or ethyl methylacrylate in a ratio of about 1:1. Typical products include Endragit L, e.g. L 100–55, marketed by Rohm GmbH, Darmstadt, Germany.

Typical cellulose acetate phthalates have an acetyl content of 17–26% and a phthalate content of from 30–40% with a viscosity of ca. 45–90 cP.

Typical cellulose acetate trimellitates have an acetyl content of 17–26%, a trimellityl content from 25–35% with a viscosity of ca. 15–20 cS. An example of an appropriate cellulose acetate trimellitate is the marketed product CAT (Eastman Kodak Company, USA).

Hydroxypropyl methylcellulose phthalates, typically have a molecular weight of from 20,000 to 100,000 daltons e.g. 80,000 to 130,000 daltons, e.g. a hydroxypropyl content of from 5 to 10%, a methoxy content of from 18 to 24% and a phthalyl content from 21 to 35%.

An example of an appropriate cellulose acetate phthalate is the marketed product CAP (Eastman Kodak, Rochester N.Y., USA).

Examples of suitable hydroxypropyl methylcellulose phthalates are the marketed products having a hydroxypropyl content of from 6–10%, a methoxy content of from 20–24%, a phthalyl content of from 21–27%, a molecular weight of about 84,000 daltons known under the trade mark HP50 and available from Shin-Etsu Chemical Co. Ltd., Tokyo, Japan, and having a hydroxypropyl content, a methoxyl content, and a phthalyl content of 5–9%, 18–22% and 27–35% respectively, and a molecular weight of 78,000 daltons, known under the trademark HP55 and available from the same supplier.

A preferred coating is HP 50.

The enteric coating may be carried out in conventional manner, e.g. so that the cores are sprayed with a solution of the enteric-coating.

Suitable solvents for the enteric-coating are for example organic solvents, e.g. an alcohol such as ethanol, a ketone such as acetone, halogenated hydrocarbons such as $CH_2Cl_2$ or mixtures of such solvents, e.g. ethanol/acetone, e.g. 1:1 to 10:1.

Conveniently a softener such as di-n-butylphthalate or triacetin is added to such a solution, e.g. in a ratio of coating material to softener of from 1: about 0.05 to about 0.3.

If desired for cellulose phthalates and other acidic coating materials an ammonium salt may be found and an aqueous solution may be used.

A fluidized bed coater may be used for coating.

Conveniently the cores are treated at room temperature or warmed up to 40° C. e.g. by means of warm air of 40° up to 70° C., before spraying. To avoid a sticking of the cores the spray procedure is preferably interrupted at certain time intervals and the cores then warmed up again. It is, however, also possible to proceed without interruption of the spray procedure, e.g. by automatic regulation of the spray amount taking into account the temperature of exhaust air and/or cores.

The spray pressure may vary within wide ranges, in general satisfactory results are obtainers with a spray pressure of from about 1 to about 1.5 bar.

The compositions of the invention are useful as immunosuppressants as indicated by standard tests.

The activity and characteristics of the compositions of the invention may be indicated in standard a) clinical trials, e.g. observing the first acute rejection episodes or treatment failure six months after transplant of kidneys or maintaining a rejection—free state within 6 months after imitation of treatment with the invention. The compositions of the invention are administered at a dose in the range of 0.5 to 2.0 g/day e.g. about 1.5 g/day and decrease the acute rejection rates when administered during the period around transplant surgery, and maintain a rejection-free state in patients who are 3 months or more after transplantation. Thus the compositions of the invention may be administered during the initial 72 hours after transplantation at dose of about 0.5 g administered twice a day in combination with a conventional steroid and cyclosporin, e.g. as NEORAL for which the cyclosporin dose is the conventional dose e.g. ca. 8±3 mg/kg for renal transplants. The steroid dose is to be administered at about 2.5 mg/kg for 4 days after transplant, 1 mg/kg thereafter for 1 week, 0.6 mg/kg thereafter for 2 weeks thereafter 0.3 mg/kg for 1 month for prednisone.

and in b) animal trials e.g. observing the kidney allograft reaction in rat. In this test one kidney from a female fisher 344 rat is transplanted onto the renal vessel of a unilaterally (left side) nephrectomized WF recipient rat using an end-to-end anastomosis. Ureteric anastomosis is also end-to-end. Treatment commences on the day of transplantation and is continued for 14 days. A contralateral nephrectomy is done seven days after transplantation, leaving the recipient relying on the performance of the donor kidney. Survival of the graft recipient is taken as the parameter for a functional graft. Typical doses of the compositions of the invention are from about 1 to 30 mg/kg p.o.

The compositions of the invention are particularly useful for the following conditions:

a) Treatment and prevention of native or transgenic organ, tissue or cellular allograft or xenograft transplant rejection, e.g. for the treatment of recipients of e.g. heart, lung, combined heart-lung, liver, kidney, pancreatic, skin, pancreatic islet cell, neural cell or corneal transplant; including treatment and prevention of acute rejection; treatment and prevention of hyperacute rejection, e.g. as associated with xenograft rejection; and treatment and prevention of chronic rejection, e.g. as associated with graft-vessel disease. The compositions of the invention are also indicated for the treatment and prevention of graft-versus-host disease, such as following bone marrow transplantation.

b) Treatment and prevention of autoimmune diseases, e.g. immune-mediated diseases and inflammatory conditions, in particular inflammatory conditions with an etiology including an immunological component such as arthritis (for example rheumatoid arthritis, arthritis chronica progrediente and arthritis deformans) and rheumatic diseases. Specific immune-mediated diseases for which the compositions of the invention may be employed include, autoimmune hematological disorders, including, but not limited to hemolytic anaemia, aplastic anaemia, pure red cell anaemia and idiopathic thrombocytopenia), systemic lupus erythematosus, polychondritis, sclerodoma, Wegener granulosis, dermatomyositis, polymyositis, chronic active hepatitis, primary bilary cirrhosis, myasthenia gravis, psoriasis, Steven-Johnson syndrome, pemphigus, idiophatic sprue, inflammatory bowel diseases (including e.g. ulcerative colitis and Crohn's disease), endocrine ophthalmophathy, Graves disease, sarcoidosis, multiple sclerosis, primary biliary cirrhosis, juvenile diabetes (diabetes mellitus type I), non-infectious uveitis (anterior and posterior), keratoconjunctivitis sicca and vernal keratoconjunctivitis, interstitial lung fibrosis, psoriatic arthritis, vasculitides, glomerulonephritides (with and without nephrotic syndrome, e.g. including idiophatic nephrotic syndrome or minimal change nephropathy) and juvenile dermatomyositis.

Appropriate dosages of the compositions of the invention will of course vary, e.g. depending on the condition to be treated (for example the disease type or the nature of resistance), the MPA salt used, the effect desired and the mode of administration.

In general however satisfactory results are obtained on administration e.g. orally at dosages on the order of from about 1 to about 30 mg salt per kg animal body weight per day, administered once or in divided doses up to 4 times per day. Suitable daily dosages for patients are thus in the order of 200 mg to 3 g p.o. salt e.g. from about 50 to 100% that of mycophenolate mofetil. For the preferred mono sodium salt the dosage of the salt is about two thirds that of mycophenolate mofetil.

Representative unit dosage forms contain from about 50 mg, e.g. 100 mg, to about 1.5 g of the pharmaceutically acceptable mycophenolate salt.

The bioavailability characteristics of compositions of the invention may be determined in conventional manner, e.g. by oral administration to beagle dogs. Dosages are typically 50 mg salt animal e.g. ca 3–5 mg salt/kg animal body weight. Dogs are adult (ca. 10 kg e.g. 6–14 kg) and fasted. Three hours after administration ca. 200 g food is administered. Blood samples are taken from the cephalic vein, before administration and 10, 30, and 45 minutes, 1, 1.5, 2, 3, 4, 6, 8, 12, and 24 hours, after administration. Plasma levels of free MPA are determined by HPLC analysis (with UV detection).

In a relative bioavailability trial as described above in male beagle dogs dosages of 3.8 mg salt/kg animal body weight p.o. were administered with the Example 1 composition as described hereinafter and with a MPA or MMF formulation corresponding to the Example 1 composition but containing an identical amount of MPA or commercially available MMF.

Results are as follows:

|  | Ex 1 | MPA | MMF |
|---|---|---|---|
| MPA (AUC Relative Bioavailability, Frel [ng · hr · ml$^{-1}$] |  |  |  |
| Mean | 4612 (218) | 3579 (174) | 2709 (100) |
| Median | 4204 (168) | 2911 (182) | 2513 (100) |
| SD | 939 | 1889 | 1363 |
| CV | 20 | 53 | 50 |
| Cmax [ng/ml] (Relative Cmax) |  |  |  |
| Mean | 5391 (313) | 3683 (227) | 2052 (100) |
| Median | 5359 (367) | 2719 (172) | 1462 (100) |
| SD | 1847 | 2504 | 945 |
| CV (%) | 34 (46) | 68 (87) | 46 (0) |

The coefficients of variation (CV) of AUC (20%) and Cmax (34%) of the Example 1 composition are significantly less than those of the reference compositions, indicating less inter-subject and intra-subject variability with the Example 1 composition.

The area under the curve (AUC) and Cmax with the Example 1 composition are higher than those of the reference compositions.

Naturally the advantageous bioavailability characteristics of the present compositions may be ascertained in standard clinical bioavailability trials. For example, doses from 200 mg to 1.5 g of the Example 1 composition and MPA, and MMF may be administered to 12 healthy volunteers in single doses in a cross-over trial. Increased AUC and $C_{max}$ may be observed for the Example 1 composition.

The compositions of the present invention are surprisingly tolerated better than MMF, inducing less gastro-intestinal side effects such as diarrhoea and burning. They show less long term side effects e.g. in the colon.

The compositions of the invention may be administered as the sole active ingredient or with another immunosuppressant e.g. together with simultaneous or separate administration of other immunosuppressants, for example, in immunosuppressive applications such as prevention and treatment of graft vs. host disease, transplant rejection, or immune-mediated disease, the compositions of the invention may be used in combination with cyclosporins or ascomycins, or their immunosuppressive analogs, e.g. cyclosporin A; FK-506 (tacrolimus), etc., rapamycin; corticosteroids; cyclophosphamide; azathioprine; methotrexate; brequinar; leflunomide; mizoribine; deoxyspergualin; analogues thereof, and immunosuppressive monoclonal antibodies, e.g., monoclonal antibodies to leukocyte receptors, e.g. MHC, CD2, CD3, CD4, CD7, CD25, CD28, CTLA4, B7, CD45, or CS58 or their ligands; or other immunomodulatory compounds.

When the compositions of the invention are co-administered with such other immunosuppressants the dosages of the other immunosuppressants may be reduced e.g. to one-half to one-third their dosages when used alone.

Representative doses for ciclosporin to be used are e.g. 1 to 10, e.g. 1 to 2 mg/kg/day.

The present invention provides in another aspect the use, method and compositions as defined hereinafter in the claims.

Insofar as details of excipients are not described herein, these are known, or available e.g. in the Handbook of Pharmaceutical Excipients, Second Edition, edited by Ainley Wade and Paul J. Weller, American Pharmaceutical Association, Washington, USA and Pharmaceutical Press, London; and Lexikon der Hilfsstoffe fur Pharmazie, Kosmetik and angrenzende Gebiete edited by H. P. Fiedler, 4th Edition, Edito Cantor, Aulendorf and earlier editions.

Following is a description by way of example only of compositions of this invention:

EXAMPLE 1

Composition
Capsule Contents

| MPA mono sodium salt | 53.43 mg (= 50 mg MPA) |
|---|---|
| Lactose (1:1 mixture of 100/200 mesh) | 256.57 mg |
| Silica (Aerosil) | 3.1 mg |
| Magnesium stearate | 1.55 mg |
|  | 314.65 mg |

Capsule is Size 1

| Enteric Coating (ca 17 mg) | |
|---|---|
| Hydroxypropyl methyl cellulose phthalate (HP50) | 9 parts |
| Triacetin | 1 part |

Procedure

The capsule ingredients are mixed and filled into size 1 capsules. The capsules are coated in a fluidized bed coater with a solution of the enteric coating ingredients in ethanol (containing 10% acetone). The coating on each capsule is about 17 mg. The capsules meet the enteric coating test described herein and do not disintegrate within 2 hours in artificial gastric juices (pH 1, HCl). The compositions are stable, e.g for 2 years at room temperature, If desired larger capsules containing 534.3 mg MFA mono sodium salt may be made in analogous manner, reducing the amount of lactose. These are well tolerated in clinical trials.

EXAMPLE 2

Capsules of size 1 are made up as in Example 1. A solution for enteric coating was made up as follows:

| | |
|---|---|
| Hydroxypropyl methyl cellulose phthalate (HP50) | 270 g |
| Triacetin | 30 g |
| Acetone | 900 g |
| Ethanol | 1800 g |

600 g of this enteric coating solution was used for 1 kg of capsules (ca. 2400). The amount of coating applied to each capsule was about 25 mg giving a film thickness of 5–6 mg/cm$^2$.

What is claimed is:

1. A pharmaceutical composition comprising a mycophenolate salt, the composition being adapted to prevent release of mycophenolate in the stomach.

2. The composition of claim 1 wherein the composition has an enteric coating and said enteric coating comprises cellulose acetate phthalate and trimellitate, or methacrylic acid copolymers containing at least 40% methacrylic acid, or hydroxypropyl methylcellulose phthalate.

3. The composition of claim 2 wherein said coating comprises methacrylic acid copolymers containing at least 40% methacrylic acid.

4. The composition of claim 2 wherein said composition is in a tablet form.

5. The composition of claim 4, wherein said tablet has a hardness between 10 and 70 N.

6. The composition of claim 2 wherein said composition is in a granule or pellet form.

7. The composition of claim 6 wherein said granule or pellet is contained in a capsule.

8. The composition of claim 1 wherein said salt is a mono-sodium salt.

9. The composition of claim 8 wherein said salt is in crystalline form.

10. The composition of claim 1 wherein said composition comprises from about 50 mg to 1.5 g of a pharmaceutically acceptable mycophenolate salt.

11. A pharmaceutical composition comprising a mycophenolate mono-sodium salt, the composition being adapted to prevent release mycophenolate in the stomach, wherein said composition has an enteric coating and said enteric coating comprises cellulose acetate phthalate and trimellitate, or methacrylic acid copolymers containing at least 40% methacrylic acid, or hydroxypropyl methylcellulose phthalate.

12. The composition of claim 11 wherein said mono-sodium salt is in crystalline form.

13. The composition of claim 11 herein said composition is in a tablet form and said tablet form has a hardness between 10 and 70 N.

14. The composition of claim 11 wherein said composition comprises from about 50 mg to 1.5 of a pharmaceutically acceptable mycophenolate salt.

* * * * *

UNITED STATES PATENT AND TRADEMARK OFFICE
CERTIFICATE OF CORRECTION

PATENT NO. : 6,306,900 B1
DATED : October 23, 2002
INVENTOR(S) : Haeberlin et al.

It is certified that error appears in the above-identified patent and that said Letters Patent is hereby corrected as shown below:

<u>Column 8,</u>
Line 26, should read: -- The composition of claim 11 wherein said composition --.
Line 30, should read: -- tion comprises from about 50 mg to 1.5 g of a pharmaceuti- --.

Signed and Sealed this

Twenty-fourth Day of December, 2002

JAMES E. ROGAN
*Director of the United States Patent and Trademark Office*